United States Patent [19]
Sugiya et al.

[11] Patent Number: 5,925,784
[45] Date of Patent: Jul. 20, 1999

[54] BIS (1,1,3,3-TETRAMETHYLBUTYL) PHOSPHINIC ACID COMPOUND, A PRODUCTION METHOD THEREOF AND AN EXTRACTING AGENT

[75] Inventors: Masashi Sugiya; Tsutomu Watanabe; Kaoru Takeuchi, all of Tokyo, Japan

[73] Assignee: Nippon Chemical Industrial Co., Ltd., Tokyo, Japan

[21] Appl. No.: 08/607,454

[22] Filed: Feb. 27, 1996

[30] Foreign Application Priority Data

Mar. 7, 1995 [JP] Japan ................... 7-072504

[51] Int. Cl.⁶ ................... C07F 5/02; C01G 1/00
[52] U.S. Cl. ................... 562/8; 423/139
[58] Field of Search ................... 562/8; 423/139

[56] References Cited

U.S. PATENT DOCUMENTS

| | | | |
|---|---|---|---|
| 3,401,185 | 9/1968 | Meinhardt | 562/8 |
| 4,069,247 | 1/1978 | Kleiner | 562/8 |
| 4,321,213 | 3/1982 | Robertson | 562/8 |
| 4,353,883 | 10/1982 | Rickelton et al. | 423/139 |
| 4,374,780 | 2/1983 | Robertson | 562/8 |
| 4,721,605 | 1/1988 | Brown et al. | 423/139 |
| 4,810,425 | 3/1989 | Nelson | 562/8 |
| 5,028,403 | 7/1991 | Rickelton et al. | 423/139 |
| 5,332,531 | 7/1994 | Horwitz et al. | 588/20 |

FOREIGN PATENT DOCUMENTS 0 236 542  9/1987  European Pat. Off. .

OTHER PUBLICATIONS

Chemical Abstracts, vol. 105, No. 4, Jul. 28, 1986, AN 027671, JP 61–044139t, Mar. 3,1986.

Laskorin et al, "Extraction of Plutonium and Uranium by Tertiary Aliphatic Phosphine Oxide", Chem.Abs. No. 86:9781, (1977).

*Primary Examiner*—Deborah C. Lambkin
*Attorney, Agent, or Firm*—Oblon, Spivak, McClelland, Maier & Neustadt, P.C.

[57] ABSTRACT

A bis(1,1,3,3-tetramethylbutyl)phosphinic acid compound represented by the formula (1) and an extracting agent using the same for separating Co from an aged electroless Ni plating solution. A di(1,1,3,3-tetramethylbutyl)phosphine is produced by carrying out a reaction between phosphine and trimethylpentene in the presence of an organic solvent and a catalyst, then said phosphine is reacted with an oxydizing agent or sulfur to obtain the compound (1):

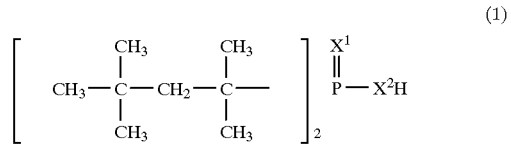

(wherein $X^1$ and $X^2$ are O or S).

5 Claims, No Drawings

BIS (1,1,3,3-TETRAMETHYLBUTYL) PHOSPHINIC ACID COMPOUND, A PRODUCTION METHOD THEREOF AND AN EXTRACTING AGENT

BACKGROUND OF THE INVENTION

The present invention relates to a bis(1,1,3,3-tetramethylbutyl)phosphinic acid compound. The present invention also relates to a method of extracting and separating cobalt and/or nickel which is contained in an aged electroless nickel plating solution. In particular, it relates to a method of selectively separating cobalt and/or nickel which is contained in an aged electroless nickel plating solution in a large amount, with a bis(1,1,3,3-tetramethylbutyl) phosphinic acid compound.

Currently, electroless plating technique finds extensive application in various fields such as production of ornamental plated articles and production of functional electronic components including magnetic discs and magnetic tapes. Regarding the metals to be plated, in addition to the nickel which has been heavily used so far, nickel-cobalt alloy has also been used in part.

Electroless plating is generally carried out by immersing a base material to be plated in a plating solution of an initially made-up plating bath, to undergo reaction for an empirically determined length of time. However, even though the plating bath and process conditions are properly controlled for the treatment, the increase of the oxidation product during the reaction is unavoidable, and the treatment solution which has been used to some extent becomes not re-usable any more. Accordingly, the solution which has been subjected to a predetermined level of plating reaction is often discarded as an aged plating solution, even though a large amount of a plating metal ion such as $Ni^{2+}$, accompanying Co which cannot be separated from Ni, and a reducing component such as sodium hypophosphite still remain in the solution.

It has been difficult so far to separate nickel from cobalt. As one such separating method, a solvent extraction process utilizing a dialkyl phosphinic acid compound derived from a dialkyl phosphine has been known (Japanese Patent Laid-Open Sho 57-73412, Japanese Patent Laid-Open 57-73143, Japanese Patent Laid-Open 61-44139, Japanese Patent Laid-Open 1-315384, and Japanese Patent Laid-Open 6-264156.)

However, a bis(1,1,3,3-tetramethylbutyl)phosphinic acid compound of the present invention is not disclosed in the above-mentioned publications, and a method of separating cobalt and nickel contained in an aged electroless nickel plating solution has not yet been known.

As a phosphinic acid compound, bis(2,4,4-trimethylpentyl) phosphinic acid which is represented by the following formula (5) and a production method thereof are disclosed (U.S. Pat. No. 4,374,780).

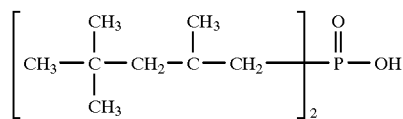

(5)

According to the method of producing the dialkylphosphinic acid specified in that patent, phosphine and diisobutylene (a mixture of 2,4,4-trimethylpentene-1 in an amount of 70%, and 2,4,4-trimethylpentene-2 in an amount of 30%) are reacted by using a free-radical catalyst to produce a dialkyl phosphine, then said product is reacted with an oxydizing agent to produce a dialkylphosphinic acid.

However, radical addition reaction in the reaction between said phosphine and diisobutylene has no reaction selectivity, and generally a mixture of mono, di-, and tri-alkylphosphines is produced. Accordingly, it is difficult to increase the generation ratio of the dialkylphosphine selectively. Thus, the yield of the dialkylphosphinic acid which is derived from the dialkyl phosphine according to above-mentioned reaction has been low.

In view of above-mentioned facts, the present inventors as a result of carring out an intensive study to find a phosphinic acid compound which is useful as an extracting agent for metals such as cobalt, and discovered that a bis(1,1,3,3-tetramethylbutyl) phosphinic acid, which is a new dialkylphosphinic acid compound, a production method thereof and its usefulness thereof as an extracting agent for metals to complete the present invention.

Further, the present inventors found that said new bis-(1,1,3,3-tetramethylbutyl)phosphinic acid compound is useful as an extracting agent for cobalt and/or nickel contained in an aged electroless nickel plating solution and completed the present invention.

SUMMARY OF THE INVENTION

It is therefore an object of the present invention is to provide a bis(1,1,3,3-tetramethylbutyl)phosphinic acid compound which is represented by the following general formula (1):

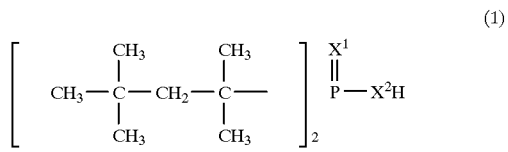

(1)

(wherein $X^1$ and $X^2$ represent an oxygen atom or a sulfur atom, and $X^1$ and $X^2$ can be the same or different).

Another object of the present invention is to provide a method of producing a bis(1,1,3,3-tetramethylbutyl) phosphinic acid compound which is represented by the following general formula (1):

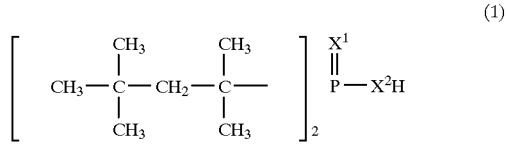

(1)

(wherein $X^1$ and $X^2$ refer to the same group as defined above), wherein di(1,1,3,3-tetramethylbutyl)phosphine which is represented by the following general formula (3):

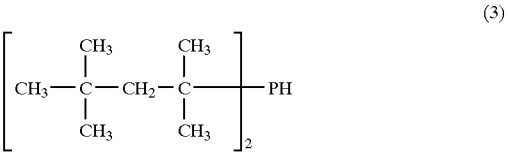

(3)

is produced by carrying out a reaction between phosphine and trimethylpentene in the presence of an organic solvent and an alkanesulfonic acid, as a catalyst, which is represented by the following general formula (2):

(wherein R represents an alkyl group having 1 to 4 carbon atoms), then said di(1,1,3,3-tetramethylbutyl)phosphine (3) is allowed to react with an oxydizing agent or sulfur.

Still another object of the present invention is to provide a method of producing a bis(1,1,3,3-tetramethylbutyl) phosphinic acid compound which is represented by the following general formula (1):

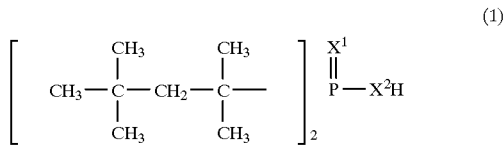

(wherein $X^1$ and $X^2$ refer to the same group as defined above), wherein di(1,1,3,3-tetramethylbutyl)phosphine which is represented by the following general formula (3):

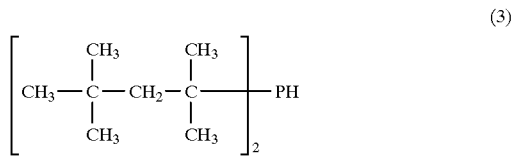

is produced by carrying out a reaction between phosphine and trimethylpentene in the presence of an organic solvent and an alkanesulfonic acid, as a catalyst, which is represented by the following general formula (2):

(wherein R refers to the same group as defined above), then said di(1,1,3,3-tetramethylbutyl)phosphine is allowed to react with an oxydizing agent or sulfur to produce bis(1,1,3,3-tetramethylbutyl)phosphine oxide or sulfide, which is represented by the following general formula (4):

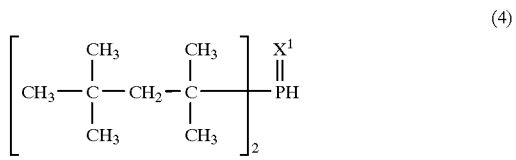

(wherein $X^1$ refers to the same group as defined above), then said bis(1,1,3,3-tetramethylbutyl)phosphine oxide or sulfide is allowed to react with an oxydizing agent or sulfur.

A further object of the present invention is to provide an extracting agent for a metal comprising the bis(1,1,3,3-tetramethylbutyl)phosphinic acid compound mentioned above.

Another object of the present invention is to provide a method of separating cobalt and/or nickel contained in an aged electroless nickel plating solution wherein an organic solvent containing an extracting agent comprising the above-mentioned bis(1,1,3,3-tetramethylbutyl)phosphinic acid compound is contacted and mixed with an aged electroless nickel plating solution containing cobalt and nickel, so that cobalt and/or nickel is selectively extracted and separated from the aged solution into the organic solvent phase.

According to the present invention, it is preferable that an organic solvent phase containing cobalt and/or nickel which is extracted in the above-mentioned manner is contacted with an aqueous solution containing a mineral acid, so that cobalt and/or nickel is transferred into the aqueous phase by back-extraction and recovered.

DETAILED DESCRIPTION OF THE INVENTION

The present invention will now be described in detail.

The bis(1,1,3,3-tetramethylbutyl)phosphinic acid compound which is represented by the above-mentioned formula (1) includes bis(1,1,3,3-tetramethylbutyl)phosphinic acid, bis(1,1,3,3-tetramethylbutyl)monothiophosphinic acid, and bis(1,1,3,3-tetramethylbutyl)dithiophosphinic acid.

According to the method of producing the bis(1,1,3,3-tetramethylbutyl)phosphinic acid compound of the present invention, the following method ① and the following method ② can be employed.

Production method ① is a method wherein as the first reaction, a reaction between the phosphine and trimethylpentene is carried out in the presence of an organic solvent and an alkanesulfonic acid, as a catalyst, to produce di(1,1,3,3-tetramethylbutyl)phosphine;

then, as the second reaction, a reaction between the produced di(1,1,3,3-tetramethylbutyl)phosphine and an oxydizing agent or sulfur is carried out to produce a bis(1,1,3,3-tetramethylbutyl)phosphinic acid compound.

The second reaction of the above-mentioned production method ① can be represented by general formulae as follows;

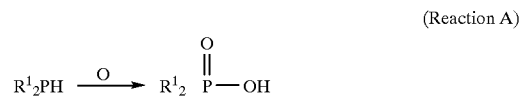
(Reaction A)

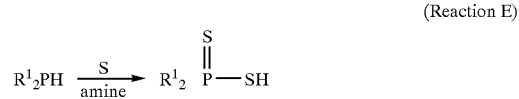
(Reaction E)

(wherein, $R^1$ represents 1,1,3,3-tetramethylbutyl group)

Production method ② is a method wherein as the first reaction, a reaction between the phosphine and trimethylpentene is carried out in the presence of an organic solvent and an alkanesulfonic acid, as a catalyst, to produce di(1,1,3,3-tetramethylbutyl)phosphine;

then, the second reaction is carried out by the following two steps;

firstly, in the first step of the second reaction, the produced di(1,1,3,3-tetramethylbutyl)phosphine is allowed to react with an oxidizing agent or sulfur to produce bis(1,1,3,3-tetramethylbutyl)phosphine oxide or sulfide;

then, in the second step of the second reaction, the produced bis(1,1,3,3-tetramethylbutyl)phosphine oxide or sulfide is allowed to react with an oxidizing agent or sulfur to produce a bis(1,1,3,3-tetramethylbutyl)phosphinic acid compound.

In the second reaction of the above-mentioned production method ②, it is preferable to carry out a reaction between bis(1,1,3,3-tetramethylbutyl)phosphine oxide or sulfide and sulfur in the presence of an amine, since the yield of the reaction can be increased when the reaction is carried out in the presence of an amine.

In the second reaction of the above-mentioned production method ②, there are three reaction paths, illustratively.

Thus the reaction can be represented by the general formulae as follows:

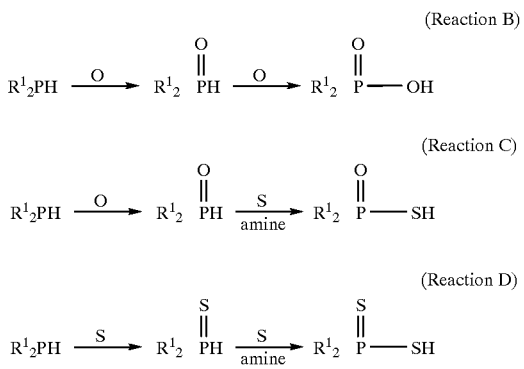

(wherein R¹ refers to the same group as defined above.)

In the first reaction of the present invention, phosphine (PH₃) obtained by any method can be used as the raw material. For example, phosphine gas obtained by refining (hydrating, removing arsine and lower hydride compound of phosphorus) of crude phosphine by-produced in soda hypophosphite production, phosphine gas compressed under high pressure, or liquefied phosphine and the like can be employed, however, phosphine as the raw material is not particularly limited to those substances.

The other raw material used in the first reaction of the present invention, trimethylpentene, is not particularly limited to any substance as far as it is industrially available, however, illustratively, 2,4,4-trimethylpentene-1, 2,4,4-trimethylpentene-2 and diisobutylene (which is a mixture of 2,4,4-trimethylpentene-1 (A) and 2,4,4-trimethylpentene-2 (B)) are preferable. A substance which is particularly preferable from the industrial viewpoint is diisobutylene, due to its low prince, but the ratio of isomers (the mixing ratio of 2,4,4-trimethylpentene-1 (A) and 2,4,4-trimethylpentene-2 (B)) varies among manufacturing companies, for example, (A):(B) may be 75:25 (%), 78:22 (%) or 70:30 (%). According to the present invention, however, the mixing ratio is not particularly limited.

As an alkanesulfonic acid, which is used as a catalyst in the first reaction of the present invention, a lower alkanesulfonic acid having 1 to 4 carbon atoms which is represented by the following general formula (2):

P—SO₃H    (2)

(wherein, R refers to the same group as defined above), can be preferably employed and illustrative examples thereof include methanesulfonic acid, ethanesulfonic acid, propanesulfonic acid, butanesulfonic acid and the like. These can be used in the form of a simple substance, a mixture of two or more kinds, an anhydride or an aqueous solution.

The first reaction in the method ① or ② of the present invention is carried out in the presence of an organic solvent, and as the organic solvent to be used for the present invention, a saturated hydrocarbon which is industrially easily available is preferable. Illustrative examples thereof include n-pentane, n-hexane, isohexane, n-pentane, n-octane, n-isooctane, n-decane, petroleum ether, petroleum benzene, ligroin, petroleum spirit, petroleum naphtha, cyclohexane, methyl cyclohexane, benzene, toluene, xylene, and ethylbenzene, and preferable examples are toluene, benzene, n-hexane and the like.

The reaction can be carried out as far as it is in the presence of an organic solvent, and the system can be made of an organic solvent alone or a mixed system of an organic solvent and water. The water can be given from the diluting solvent for the catalyst, when water is used as the diluting solvent, or the water can be added independently at an arbitrary rate.

As for the first reaction in the method ① or ② of the present invention, the reaction between phosphine and trimethylpentene in the presence of an alkanesulfonic acid and an organic solvent, is carried out in a pressure vessel such as an autoclave which is desirably an apparatus that is equipped with a teflon internal cylinder in order to prevent the corrosion due to the acid. The molar ratio of the phosphine to trimethylpentene is 1:2–1:5, preferably 1:2–1:3. The reaction temperature is room temperature—100° C., preferably 60–80° C., and the reaction time is normally 1–24 hours, preferably 2–10 hours.

It is desirable that the raw materials are put into the reaction vessel after the vessel is sufficiently purged with an inactive gas such as nitrogen or helium and the like, and in order to prevent the self-polymerization of trimethylpentene, it is desirable that an organic solvent, trimethylpentene and phosphine are added in this order, and after they are heated to a desired temperature, a catalyst is added under pressure.

After completion of the reaction, the mixture is cooled to room temperature and unreacted phosphine gas is replaced with an inactive gas. When water is used as a diluting solvent for the catalyst, a part of the resulting di(1,1,3,3-tetramethylbutyl)phosphine is liberated in the organic solvent, however, the most of it forms a phosphonium salt with the alkanesulfonic acid, the catalyst, in the aqueous layer, the lower layer. When an anhydrous alkanesulfonic acid is used as the catalyst, all of the product forms a phosphonium salt with the alkanesulfonic acid.

Those two layers, the organic layer and the aqueous layer are separated by the normal method. For isolating di(1,1,3,3-tetramethylbutyl)phosphine from the resulting product, di(1,1,3,3-tetramethylbutyl)phosphine is transferred into the organic phase by carrying out neutralization with an alkali aqueous solution, and the resulting organic phase is distilled under reduced pressure to give di(1,1,3,3-tetramethyl-butyl) phosphine of high purity which is almost free from any isomers.

An illustrative example of an oxidizing agent to be used in the second reaction in the method ① or ② of the present invention includes a peroxide such as hydrogen peroxide and benzoyl peroxide, a nitrogen oxide such as nitric acid, NO, N₂O₄, and N₂O, and a sulfur oxide such as SO₂ sulfuric acid, and the like, but particularly preferable from the industrial viewpoint is hydrogen peroxide.

An illustrative example of the amine, which is used in the second reaction of the present invention includes N,N-dimethylbenzylamine, benzylamine, methylamine, dimethylamine, trimethylamine, ethylamine, diethylamine, triethylamine, n-propylamine, di-n-propylamine, tri-n-propylamine, isopropylamine, n-butylamine, isobutylamine, sec-butylamine, tert-butylamine, cyclohexylamine, α-phenylethylamine, β-phenylethylamine, ethylenediamine, diamine, tetramethylenediamine, hexamethylenediamine, o-phenylenediamine, m-phenylenediamine, and p-phenylenediamine and the like.

Referring now to the subsequent second reaction in the method ① or ②, the above-mentioned Reactions A–E will be explained.

The above-mentioned reaction A comprises a reaction between di(1,1,3,3-tetramethylbutyl)phosphine obtained in the first reaction and an oxidizing agent. The procedure to be used for this reaction when di(1,1,3,3-tetramethylbutyl)

phosphine is isolated and purified in the first reaction is different from that used when di(1,1,3,3-tetramethylbutyl) phosphine forms a phosphonium salt with an alkanesulfonic acid in the aqueous layer separated from the organic layer after completion of the first reaction.

That is, when di(1,1,3,3-tetramethylbutyl)phosphine is isolated and purified, only by adding an oxidizing agent, the oxidation reaction proceeds as shown by reaction A to give bis(1,1,3,3-tetramethylbutyl)phosphinic acid, which is the desired product of the present invention.

When di(1,1,3,3-tetramethylbutyl)phosphine forms a phosphonium salt with the alkanesulfonic acid in the reaction mixture obtained in the first reaction, there are three processes for the reaction.

The first process is a process like reaction A in which a predetermined amount of an oxidizing agent is added to the reaction solution, to prepare bis(1,1,3,3-tetramethylbutyl) phosphinic acid, and isolate it from the alkylsulfonic acid.

The second process is a process like reaction B in which half the amount of the oxidizing agent which is necessary for the reaction solution, is added to prepare bis(1,1,3,3-tetramethylbutyl)phosphine oxide, then the remaining oxidizing agent is added thereto to make it bis(1,1,3,3-tetramethylbutyl) phosphinic acid. Here, it is preferable to separate the alkanesulfonic acid when the phosphine oxide is generated, and distillation purification can be carried out at the same time.

The third process is a process in which an alkali is firstly added to the reaction solution to separate the alkanesulfonic acid in the form of a metal salt, then like reaction A, an oxidizing agent is added and reacted to prepare bis(1,1,3,3-tetramethylbutyl)phosphinic acid.

Alternatively, bis(1,1,3,3-tetramethylbutyl)phosphinic acid may also be obtained by adding water and an organic solvent to the reaction solution and heating the mixture, separating alkanesulfonic acid and the reaction product, and after removing the organic solvent, oxidizing agent is added and reacted, as in the case of reaction A. In this case, the organic solvents which can be used include n-pentane, n-hexane, isohexane, n-octane, isooctane, n-decane, petroleum ether, petroleum benzine, ligroin, petroleum spirit, petroleum naphtha, cyclohexane, benzene, toluene, xylene, ethylbenzene, etc., and preferably, n-hexane, toluene, bezene, etc.

Among the above-mentioned processes, a process to give bis(1,1,3,3-tetramethylbutyl)phosphinic acid of higher purity is the second process wherein the phosphine oxide obtained in the middle of the reaction is distilled and purified. That is because, after it is made to dialkylphosphinic acid, the distillation purification cannot be carried out.

In any of the above-mentioned processes, when the reaction between di(1,1,3,3-tetramethylbutyl)phosphine and the oxidizing agent is carried out by oxidizing di(1,1,3,3-tetramethylbutyl)phosphine in the absence of a solvent, or in a solvent such as water or acetic acid, by using an oxidizing agent such as hydrogen peroxide, bis(1,1,3,3-tetramethylbutyl) phosphinic acid of high purity which is almost free from any isomers can be produced.

The amount of the oxidizing agent to be used is 2–2.2 moles, preferably 2.1–2.15 moles for 1 mole of di(1,1,3,3-tetramethylbutyl)phosphine. The reaction temperature is room temperature—100° C., preferably 50–100° C. Since the oxidation reaction is an exothermic reaction, it is preferable to carry out the reaction by controlling the dropping speed so that the temperature does not rise rapidly.

The reaction C is a process in which a predetermined amount of an oxidizing agent is added to a reaction solution containing di(1,1,3,3-tetramethylbutyl)phosphine obtained in the first reaction to produce di(1,1,3,3-tetramethylbutyl) phosphine oxide, then sulfur is allowed to react to generate bis(1,1,3,3-tetramethylbutyl)monothiophosphinic acid. As for the reaction with sulfur, it is more preferable to carry out the reaction in the presence of an amine.

The amount of an oxidizing agent to be used is preferably 1–1.2 moles, preferably 1.1–1.15 moles for 1 mole of di(1,1,3,3-tetramethylbutyl)phosphine. The reaction temperature is similar to those for the above-mentioned reactions A and B. The amount of the sulfur to be used is 1–1.2 moles, preferably 1.0–1.05 moles for 1 mole of di(1,1,3,3-tetramethylbutyl) phosphine oxide. Similarly, the amount of the amine to be used is 1–1.2 moles, preferably 1.0–1.05 moles. The reaction temperature is room temperature—100° C., preferably 30–50° C.

The reaction D is a process in which a predetermined amount of sulfur is added to a reaction solution containing di(1,1,3,3-tetramethylbutyl)phosphine obtained in the first reaction to produce di(1,1,3,3-tetramethylbutyl)phosphine sulfide, then sulfur is further added and reacted to produce bis(1,1,3,3-tetramethylbutyl)dithiophosphinic acid. It is preferable to add an amine during the reaction in which the phosphine sulfide is changed to dithiophosphinic acid.

The amount of the sulfur to be used is 2–2.2 moles, preferably 2.0–2.1 moles for 1 mole of di(1,1,3,3-tetramethylbutyl)phosphine. The amount of the amine to be used is 1.0–1.2 moles, preferably 1.0–1.05 moles for 1 mole of di(1,1,3,3-tetramethylbutyl)phosphine sulfide. The reaction temperature is room temperature—100° C., preferably 30–50° C.

The reaction E is a process in which di(1,1,3,3-tetramethylbutyl)phosphine obtained in the first reaction and sulfur are directly reacted. This reaction is carried out by adding a predetermined amount of sulfur to a reaction solution containing di(1,1,3,3-tetramethylbutyl)phosphine obtained in the first reaction to generate bis(1,1,3,3-tetramethylbutyl)dithio-phosphinic acid directly. Here, it is more preferable to carry out the reaction in the presence of an amine.

The amount of the sulfur to be used is 2–2.2 moles, preferably 2.0–2.1 moles for 1 mole of di(1,1,3,3-tetramethylbutyl)phosphine. The amount of the amine to be used is 1.0–1.2 moles, preferably 1.0–1.05 moles for 1 mole of di(1,1,3,3-tetramethylbutyl)phosphine. The reaction temperature is room temperature—100° C., preferably 30–50° C.

As for the reaction mechanism of the production method according to the present invention, in the reaction between phosphine and trimethylpentene, a proton of the alkanesulfonic acid, which is the catalyst, is added to the unsaturated bond of the olefin (trimethylpentene) to form carbonyl cation which is represented by the following formula (6), and this cation causes electrophilic addition reaction to the lone electron-pair of the phosphine.

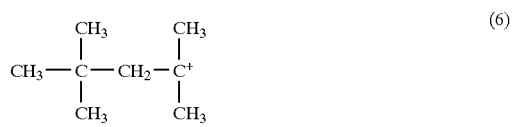

Accordingly, as the raw material, trimethylpentene, illustratively isomers of diisobutylene, 2,4,4-trimethylpentene-1 and 2,4,4-trimethylpentene-2 both form the same carbonium cation represented by the same formula (6), a dialkylphosphine [di(1,1,3,3-tetramethylbutyl)phosphine] which is almost free from isomers can be obtained. And the dialkylphosphinic acid can be easily obtained by the use of an oxidizing agent.

This means that the raw material olefin mixture can be used as it is; i.e., there is no need for the use of a single compound obtained by isolation or purification, as a raw material, and no need for any special reaction procedure such as stopping the reaction halfway, or employing an excessive charging ratio etc. Thus, a dialkylphosphinic compound of high purity which is almost free from isomers can be produced at low cost.

The bis(1,1,3,3-tetramethylbutyl)phosphinic acid compound of the present invention is useful as an extracting agent for metals contained in an aqueous solution. Illustrative examples of the metal to be extracted include rare metal elements such as cobalt, nickel, zirconium, hafnium, gallium, vanadium, and molybdenum, and rare-earth metal elements such as yttrium, samarium, and neodymium. Among these, it is particularly suited for separation of cobalt and nickel.

Extraction of the metal, illustratively cobalt and nickel, contained in the aqueous solution is carried out by contacting and mixing an organic solvent containing an extracting agent comprising bis(1,1,3,3-tetramethylbutyl) phosphinic acid compound with an aqueous solution containing cobalt and nickel, and by extracting cobalt into the organic solvent phase from the aqueous solution and keeping nickel in the aqueous phase. After removing cobalt by the extruction, pH is re-adjusted and the extruction agent is added again to transfer nickel into the organic solvent phase, so that the cobalt and the nickel are separated in turn.

The organic solvent phase containing the cobalt and/or nickel is contacted with the aqueous solution containing a mineral acid, to strip cobalt and/or nickel into the aqueous phase of the aqueous solution, and the cobalt and/or nickel is recovered from the aqueous phase.

The concentration of the extracting agent to be contained in the organic solvent depends on the concentration of the metal ion, and the phase ratio of the organic solvent phase to the aqueous phase, however, a desirable concentration is usually 3–70% by weight, preferably 5–40% by weight. A desirable pH during the extraction is 5–9, preferably 6–8.

Illustrative examples of the organic solvent to be used for the extraction include aliphatic hydrocarbons such as hexane, heptane, normal paraffin, naphthenic hydrocarbon such as 1-naphthenic acid, 2-naphthenic acid, and aromatic hydrocarbons such as kerosene and xylene.

A bis(1,1,3,3-tetramethylbutyl)phosphinic acid compound represented by the above-mentioned general formula (1) of the present invention is specifically useful as an extracting agent for separating cobalt in an aged electroless nickel plating solution.

The aged electroless nickel plating solution to be treated according to the present invention is mainly a waste nickel plating solution containing sodium hypophosphite as a reducing agent, however, this method can also be applied to a waste plating solution containing nickel-cobalt alloy as the plating metal source.

In an initially made-up plating bath used for electroless nickel plating, sodium hypophosphite which is used as a reducing agent is gradually oxidized and becomes sodium phosphite during electroless plating process, thus the plating activity is degraded, and even though a newly prepared plating solution is replenished so that the resulting plating bath contains a considerable amount of $Ni^{2+}$, the plating bath does not exhibit the plating activity any more. A waste plating solution refers to a plating bath solution which shall be discarded since it does not exhibit the plating activity any more. The waste plating solution also contains a large amount of cobalt ion which accompanies Ni ion and which is not separated from Ni ion.

The composition of the aged electroless nickel plating solution differs according to the plating bath compositions and plating conditions, however, an aged nickel plating solution is, illustratively, an aqueous solution generally containing Ni2+ in an amount of 4–7 g/L, $Co^{2+}$ in an amount of 0.001–1.0 g/L, $H_2PO_2^{2-}$ in an amount of 25–55 g/L, $HPO_3^{2-}$ in an amount of 80–100 g/L, $SO_4^{2-}$ in an amount of 30–75 g/L, and a chelating agent in an amount of 30–55 g/L. The aged electroless nickel plating solution to be treated according to the present invention is not limited to the aged solution having the above-mentioned composition.

The aged electroless nickel plating solution is generally an acid solution the pH of which is close to 4.5. According to the present invention, the pH is controlled to be in the range of pH 3 to 9, preferably 4 to 8 wherein the cobalt and/or nickel is extracted. The controlling of pH can be carried out by adding a solution of a commonly used alkaline agent such as sodium hydroxide, potassium hydroxide, and ammoniacal water.

The extracting agent to carry out solvent extraction of the cobalt and/or nickel according to the present invention is a bis(1,1,3,3-tetramethylbutyl)phosphinic acid compound represented by the above-mentioned general formula (1), and illustrative examples include bis(1,1,3,3-tetramethylbutyl) phosphinic acid, bis(1,1,3,3-tetramethylbutyl)monothio phosphinic acid, and bis(1,1,3,3-tetramethylbutyl)dithio phosphinic acid.

The method of extraction is generally carried out through two-step procedure. Firstly, an organic solvent containing an extracting agent which comprises a bis(1,1,3,3-tetramethylbutyl) phosphinic acid compound with an aged electroless nickel plating solution containing cobalt and nickel, extracting the cobalt into the organic solvent phase from the aqueous aged solution, and separating the cobalt and the nickel. Secondly, the aqueous; phase from which cobalt was removed out is diluted with pure water 2 to 10 fold, and mixed with extruction agent which is a mixture of bis(1,1,3,3-tetramethylbutyl) phosphinic acid compound and phosphoric diester to extruct and separate nickel into organic phase.

A dilution ratio of the aqueous phase when nickel extruction is carried out, depends on the amount of phosphorous ion, hypophosphorous ion, sulfuric ion, etc. Molar ratio of phosphinic acid: phosphoric diester is 100:1 to 1:1, preferably 50:1 to 10:1. And the phosphoric diester includes di(2-ethylhexyl)phosphate, di(n-decyl)phosphate, di(hexadecyl)phosphate, di(benzyl)phosphate, etc., preferably, di(2-ethylhexyl)phosphate.

As for carrying out the contact, a method utilizing a multi-stage continuous extractor such as mixer-settler is industrially preferable since a large amount of the aged solution can be continuously treated.

The organic solvent phase containing the extracted cobalt and/or nickel is contacted with an aqueous solution containing a mineral acid to transfer the cobalt and/or nickel into the aqueous phase of the aqueous solution, then the cobalt and/or nickel is recovered from the aqueous phase.

The concentration of a bis(1,1,3,3-tetramethylbutyl) phosphinic acid compound to be contained in the organic solvent depends on the metal ion concentration, and the phase ratio of the organic solvent phase to the aqueous phase, however, it is normally 3–70% by weight, preferably 5–40% by weight.

The mixing ratio at which the aged electroless nickel plating solution (A) is mixed with an organic solvent (B) containing a bis(1,1,3,3-tetramethylbutyl)phosphinic acid compound as the extracting agent is normally A:B=20:1–1:20 (by volume) and preferably 5:1–1:5 (by volume).

The temperature at which the extraction is carried out is 10–100° C., preferably 20–70° C.

Illustrative examples of the organic solvent to be used for extraction include aliphatic hydrocarbons such as hexane, heptane, and normal paraffin, naphthenic hydrocarbons such as 1--naphthenic acid, and 2-naphthenic acid, and aromatic hydrocarbons such as kerosene and xylene. These organic solvents can be used alone or two or more such compounds can be used in mixture.

According to the present invention, it is desirable to add an additive such as a higher alcohol or a neutral phosphoric ester to the extraction system in order to improve the percent extraction of the cobalt.

Illustrative examples of the higher alcohol include isodecanol, 1-octanol, 2-octanol, 2-ethyl-1-hexanol, 1-nonanol, 1-undecanol, 1-dodecanol, cyclopentanol, and cyclohexanol and the like. Preferable compound is isodecanol.

Illustrative examples of the neutral phosphoric ester include tributylphosphate, butylphosphonic acid dibutyl ester, dibutylphosphine dibutyl ester, tricresyl phosphate, tributylphosphine oxide, trioctylphosphine oxide and the like. Preferable example is tributylphosphate.

A preferable amount of the above-mentioned additive is normally 2–5% by volume with respect to the extraction solvent.

EXAMPLES

To further illustrate the present invention, the following examples are given.

Example 1

An autoclave having a capacity of 1.5 L (liters) equipped with a teflon internal cylinder was sufficiently purged with nitrogen, and 224.4 g (2.0 moles) of diisobutylene (a mixture of 2,4,4-trimethyl pentene-1 in an amount of 75% and 2,4,4-trimethyl pentene-2 in an amount of 25%), and 300 ml of n-hexane were put in it, then 34.0 g (1.0 mole) of phosphine was introduced from a bomb. The mixture was heated to 80° C/, and 192.2 g (2.0 moles) of a 50% aqueous methanesulfonic acid solution was added thereto by a pressure pump for 3 hours, while the temperature was kept at 80° C. Then this was matured at 80° C. for 2 hours. The internal pressure was decreased from 15.0 kg/cm$^2$ to 5.5 kg/cm$^2$. After it was cooled to room temperature, the remaining phosphine was gradually blown into removing equipment, then the system was purged with nitrogen three times.

The reaction solution was transferred in a nitrogen atmosphere to a 3 L four-neck flask equipped with a condenser, a thermometer, a stirrer and a dropping funnel, and 320 g (2.0 moles) of a 25% aqueous sodium hydroxide solution was added dropwise while the temperature was kept at 30° C. or lower. The hexane layer was separated and washed with a 10% aqueous sodium carbonate solution, then dehydrated with anhydrous sodium sulfate and allowed to stand still for 24 hours.

After the sodium sulfate was removed, n-hexane was removed by using an evaporator and the resulting transparent colorless liquid was subjected to reduced-pressure distillation, and a fraction at 114–116° C./1.8 mmHg was separated to give 121.7 g of a colorless transparent liquid.

This substance was identified as di(1,1,3,3-tetramethylbutyl)phosphine by GC-MASS. The purity as analyzed by gas chromatograhy was 96.8%, and the substance contained a constitutional isomer in an amount of 1.1% and the yield was 45.7%.

GC-MASS: m/z=258[M]$^+$ $^1$H-NMR: (CDCl$_3$, δ) 1.00 (s,18 H), 1.37 (d, 12 H, J=11.4 Hz), 1.63 (d, 4 H, J=9.0 Hz)

FT-IR: (liquid membrane process, cm$^{-1}$) 2940 (C-H stretching), 2260 (P-13 stretching), 1465 (t-butyl asymmetrical deformation), 1360 (t-butyl symmetrical deformation), 1200 (t-butyl skeletal vibration), 1120 (P-C stretching), 800 (C-P-C deformation).

Into a 1 L four-neck flask equipped with a condenser, a thermometer, a stirrer and a dropping funnel, were added 106.6 g (0.40 moles) of di(1,1,3,3-tetramethylbutyl) phosphine obtained in the above-mentioned reaction and 300 ml of acetic acid in a nitrogen atmosphere, and 95.2 g (0.84 moles) of 30% hydrogen peroxide was added thereto dropwise at 60° C., and it was matured at 100° C. for 2 hours. After it was cooled, acetic acid was removed by using an evaporator to give 112.2 g of a white solid. This solid was identified as bis(1,1,3,3-tetramethyl-butyl) phosphinic acid by the analysis with FAB-MASS. The melting point was 101–102° C., the purity obtained by titration was 98.5%, and the yield was 95.3%.

FAB-MASS: m/z=291[M+H]$^+$ $^1$H-NMR: (CDCl$_3$, δ) 1.03 (s, 18 H), 1.40 (d, 12 H, J=16.8 Hz), 1.77(d, 4 H, J=8.4 Hz),9.94 (s,1 H)

FT-IR: (KBr, cm$^{-1}$) 2950 (C-H stretching), 1470 (t-butyl asymmetrical deformation), 1360 (t-butyl symmetrical deformation), 1145 (P=0 stretching), 925 (P-O-H stretching), 800 (C-P-C deformation).

Example 2

An autoclave having a capacity of 1.5 L equipped with a teflon internal cylinder was sufficiently purged with nitrogen, and 224.4 g (2.0 moles) of diisobutylene (a mixture of 2,4,4-trimethyl pentene-1 in an amount of 75% and 2,4,4-trimethyl pentene-2 in an amount of 25%), and 300 ml of n-hexane were put in it, then 34 g (1.0 mole) of phosphine was introduced from a bomb. The mixture was heated to 80° C., and 192.2 g (2.0 moles) of a 50% aqueous methanesulfonic acid solution was added thereto by a pressure pump for 3 hours, while the temperature was kept at 80° C. Then this was matured at 80° C. for 2 hours. The internal pressure was decreased from 15.0 kg/cm$^2$ to 5.5 kg/cm$^2$. After it was cooled to room temperature, the remaining phosphine was gradually blown into removing equipment, then the system was purged with nitrogen three times.

The resulting reaction solution was separated by a separatory funnel under a nitrogen atmosphere to give 541.2 g of a slightly yellow transparent aqueous solution. The analysis by FAB-MASS etc., showed that di(1,1,3,3-tetramethylbutyl)phosphine had formed a stable phosphonium salt with methanesulfonic acid. The aqueous solution was subjected to nonaqueous titration using an anhydrous acetic acid solution of perchloric acid. The concentration was 37.6% and the yield was 57.5%.

Into a 1 L four-neck flask equipped with a condenser, a thermometer, a stirrer and a dropping funnel, was added 470.9 g of the reaction solution [di(1,1,3,3-tetramethylbutyl) phosphine of 0.50 moles] obtained in the above-mentioned reaction, and 120.2 g (1.06 moles) of 30% hydrogen peroxide was added dropwise while the liquid temperature was kept at 60–70° C., and it was matured at 100° C. for 2 hours. The reaction solution was separated into two layers, and the product was liberated from an aqueous methanesulfonic acid solution.

The reaction solution was extracted with 300 ml of n-hexane, and washed with a 5% aqueous sodium carbonate solution, then dehydrated with anhydrous sodium sulfate and allowed to stand still for 24 hours.

The aqueous solution obtained after separating those two layers was condensed by an evaporator to give 167.8 g of methanesulfonic acid having a purity of 95.1%. It could be regenerated with a recovery rate of 95.4% and the regenerated methanesulfonic acid could be re-used in the above-mentioned first reaction.

Sodium sulfate was filtered out from the hexane solution and hexane was removed by evaporation using an evaporator to give 140.9 g of a white solid. It was identified as bis(1,1,3,3-tetramethylbutyl)phosphinic acid by analysis with FAB-MASS. (The purity obtained by titration was 96.5%, the yield was 93.6%)

Example 3

An autoclave having a capacity of 1.5 L equipped with a teflon internal cylinder was sufficiently purged with nitrogen, and 224.4 g (2.0 moles) of diisobutylene (a mixture of 2,4,4-trimethyl pentene-1 in an amount of 75% and 2,4,4-trimethyl pentene-2 in an amount of 25%), and 300 ml of n-hexane were put in it, then 34 g (1.0 mole) of phosphine was introduced from a bomb. The mixture was heated to 80° C., and 192.2 g (2.0 moles) of a 50% aqueous methanesulfonic acid solution was added thereto by a pressure pump for 3 hours, while the temperature was kept at 80° C. Then this was matured at 80° C. for 2 hours. The internal pressure was decreased from 15.0 kg/cm$^2$ to 5.5 kg/cm$^2$. After it was cooled to room temperature, the remaining phosphine was gradually blown into removing equipment, then the system was purged with nitrogen three times.

The resulting reaction solution was separated by a separatory funnel under a nitrogen atmosphere to give 541.2 g of a slightly yellow transparent aqueous solution. The analysis by FAB-MASS etc., showed that di(1,1,3,3-tetramethylbutyl)phosphine had formed a stable phosphonium salt with methanesulfonic acid. The aqueous solution was subjected to nonaqueous titration using an anhydrous acetic acid solution of perchloric acid. The concentration was 37.6%, the yield was 57.5%.

Into a 1 L four-neck flask equipped with a condenser, a thermometer, a stirrer and a dropping funnel, was added 470.9 g of the reaction solution [di(1,1,3,3-tetramethylbutyl) phosphine of 0.50 moles] obtained in the above-mentioned reaction, and 60.1 g (0.853 moles) of 30% hydrogen peroxide was added dropwise while the liquid temperature was kept at 60–70° C., and it was matured at 100° C. for 2 hours. The reaction solution was separated into two layers, and the product was liberated in the upper layer.

The upper layer was separated, and the lower layer, which is an aqueous methanesulfonic acid solution, was extracted with 300 ml of n-hexane, and the extract was added to the above-mentioned liberated upper layer. It was then washed with a 5% aqueous sodium carbonate solution, then dehydrated with anhydrous sodium sulfate and allowed to stand still for 24 hours.

The sodium sulfate was filtered out from the mixture, then hexane was removed by an evaporator to give 132.7 g of a colorless transparent viscous liquid. The liquid was subjected to reduced-pressure distillation, and a fraction at 152–154° C./3.5) mmHg was separated to give 114.8 g of a colorless transparent viscous liquid. It was identified as di(1,1,3,3-tetramethylbutyl)phosphine oxide by the analysis with GC-MASS. (The purity was 98.1%, the yield was 82.2%)

GC-MASS: m/z=274[M]$^+$ $^1$H-NMR: (CDCl$_3$, δ) 1.06 (s, 18 H), 1.41 (dd, 12 H, J=17.4, 3.6 Hz), 1.80 (dd, 4 H, J=7.8, 2.4 Hz), 5.81 (d, 1 H, J=425.1 Hz)

FT-IR: (liquid membrane process, cm$^{-1}$) 2950 (C-H stretching), 2260 (P-H stretching), 1475 (t-butyl asymmetrical deformation), 1362 (t-butyl symmetrical deformation), 1170 (P-O stretching), 1130 (P-C stretching), 800 (C-P-C deformation).

Into a 1 L four-neck flask equipped with a condenser, a thermometer, a stirrer and a dropping funnel, were added 97.8 g (0.35 moles) of di(1,1,3,3-tetramethylbutyl) phosphine oxide obtained in the above-mentioned reaction, and 300 ml of acetic acid, and 41.9 g (0.37 moles) of 30% hydrogen peroxide was added dropwise while the liquid temperature was kept at 60–70° C., and it was matured at 100° C. for 2 hours. The acetic acid was removed by evaporation using an evaporator to give 94.5 g of a white solid. It was identified as bis(1,1,3,3-tetramethylbutyl) phosphinic acid by the analysis using FAB-MASS. (The purity obtained by titration was 99.1%, the yield was 92.3%)

Example 4

Into a 1 L four-neck flask equipped with a condenser, a thermometer, a stirrer and a dropping funnel, were added 97.8 g of di(1,1,3,3-tetramethylbutyl)phosphine oxide obtained in Example 3, 300 ml of toluene, and 11.2 g (0.35 moles) of sulfur, and 47.3 g (0.35 moles) of N,N-dimethylbenzylamine was added dropwise while it was stirred at room temperature. The sulfur was decreased with the dropping, and it was matured at 60° C. for 2 hours. After it was cooled, it was extracted with an aqueous hydrochloric acid solution to remove amine, then the extract was washed with pure water and dehydrated with anhydrous sodium sulfate.

The toluene was removed by an evaporator to give 108.2 g of a white solid. The solid was identified as bis(1,1,3,3-tetramethylbutyl)monothiophosphinic acid by an analysis using FAB-MASS. The melting point was 121–122° C., the purity obtained by titration was 97.9%, and the yield was 98.8%.

FAB-MASS: m/z=307[M+H]$^+$ $^1$H-NMR: (CDCl$_3$, δ) 1.05 (s, 18 H), 1.49 (dd, 12 H, J=18.0, 1.2 Hz), 1.88 (dd, 4 H, J=9.0, 0.6 Hz)

FT-IR: (KBr, cm$^{-1}$) 2950 (C-H stretching), 1475 (t-butyl asymmetrical deformation), 1368 (t-butyl symmetrical deformation), 1240 (t-butyl skeletal vibration), 1125 (P-C stretching), 910 (P-O-H stretching), 800 (C-P-C deformation), 678 (C-P-S deformation), 620 (P=S stretching), 535 (P-S-H stretching).

Example 5

Into a 1 L four-neck flask equipped with a condenser, a thermometer, and a stirrer, were added 106.6 g (0.40 moles) of di(1,1,3,3-tetramethylbutyl)phosphine, 300 ml of toluene, and 12.8 g (0.4 moles) of sulfur under a nitrogen atmosphere, while it was stirred at room temperature, the liquid temperature rose to 35° C., then the mixture was matured at 60° C. for 2 hours. After it was cooled, it was confirmed that no unreacted sulfur was precipitated on the bottom. The toluene was removed by an evaporator to give 120.3 g of a white solid. The solid was identified as di(1,1,3,3-tetramethylbutyl)monothiophosphine sulfide by the analysis using FAB-MASS. The melting point was 79–80° C., the purity obtained by titration was 95.1%, and the yield was 98.5%.

FAB-MASS: m/z=291[M+H]$^+$ $^1$H-NMR: (CDCl$_3$, δ) 1.06 (s, 18 H), 1.50 (dd, 12 H, J=18.6 Hz), 1.95 (dd, 4 H, J=16.8, 6.3 Hz), 5.90 (d, 1 H, 382.6 Hz).

FT-IR: (KBr, cm$^{-1}$) 2970 (C-H stretching), 2310 (P-H stretching), 1480 (t-butyl asymmetrical deformation), 1370 (t-butyl symmetrical deformation), 1245 (t-butyl skeletal vibration), 1125 (P-C stretching), 800 (C-P-C deformation), 680 (C-P-S deformation), 632 (F=S stretching).

Into a 1 L four-neck flask equipped with a condenser, a thermometer and a stirrer, were added 91.6 g (0.30 moles) of di(1,1,3,3-tetramethylbutyl)phosphine sulfide, 300 ml of toluene and 9.6 g (0.3 moles) of sulfur, and 40.6 g (0.3 moles) of N,N-dimethylbenzylamine was added dropwise while the solution was stirred at room temperature. The sulfur was decreased with the dropping and it was matured at 60° C. for 2 hours. After it was cooled, it was extracted with an hydrochloric acid solution to remove amine, then the extract was washed with pure water and dehydrated with anhydrous sodium sulfate.

The toluene was removed by an evaporator to give 100.5 g of a white solid. The solid was identified as bis(1,1,3,3-tetramethylbutyl)dithiophosphinic acid by an analysis using FAB-MASS. The melting point was 42–43° C., the purity obtained by titration was 95.6%, and the yield was 99.5%.

FAB-MASS: m/z=323[M+H]$^+$ $^1$H-NMR: (CDCl$_3$, δ) 1.05 (s, 18 H), 1.58 (d, 12 H, J=20.4 Hz), 1.92 (d, 4 H, J=9.6 Hz).

FT-IR: (KBr, cm$^{-1}$) 2975 (C-H stretching), 1480 (t-butyl asymmetrical deformation), 1370 (t-butyl symmetrical deformation), 1240 (t-butyl skeletal vibration), 1120 (P-C stretching), 795 (C-P-C deformation), 670 (C-P-S deformation), 620 (P=S stretching), 530 (P-S-H stretching).

Example 6

Into a 1 l four-neck flask equipped with a condenser, a thermometer, and a stirrer, were added 106.6 g (0.40 moles) of di(1,1,3,3-tetramethylbutyl)phosphine, 300 ml of toluene, and 25.6 g (0.8 moles) of sulfur under a nitrogen atmosphere, and 54.1 g (0.4 moles) of N,N-dimethylbenzylamine was added dropwise while it was stirred. The sulfur was decreased with the dropping, and the mixture was matured at 60° C. for 2 hours. After it was cooled, extraction with an aqueous hydrochloric acid solution was carried out to remove amine, and the toluene layer was washed with pure water and dehydrated with anhydrous sodium sulfate.

The toluene was removed by an evaporator to give 130.4 g of a white solid. The solid was identified as bis(1,1,3,3-tetramethylbutyl)dithiophosphinic acid by an analysis using FAB-MASS. The purity obtained by titration was 98.6%, and the yield was 99.8%.

Example 7

Extraction of cobalt by solvent extraction process

Bis(1,1,3,3-tetramethylbutyl)phosphinic acid (purity obtained by titration of 98.5%) was dissolved in xylene to give a concentration of 20% by weight, and tri-n-butyl phosphate was dissolved in xylene to give a concentration of 10% by volume to prevent emulsion to prepare an extracting agent solution (O). Cobalt sulfate and nickel sulfate were so dissolved in pure water that Co (II) gave a concentration of 10.1 g/l and Ni (II) gave a concentration of 100.5 g/l to prepare a solution to be extracted (A). For adjusting the pH to a desired value, an aqueous sodium hydroxide solution was used.

Each of (A) and (O) solution was put in an Erlenmeyer flask (volumetric ratio A/O=1), and they were contacted for 10 minutes at 50° C. by a thermostatic shaker. After the mixture was separated into an organic solvent (xylene) phase and an aqueous phase, Co (II) and Ni (II) in the organic solvent phase were analyzed to obtain the extraction rate and the selectivity coefficient for each metal. The results are shown in Table 1.

TABLE 1

| | Extraction rate (E%) | | Co/Ni |
| pH | Co in organic phase | Ni in organic phase | Selectivity coefficient |
| --- | --- | --- | --- |
| 4.00 | 1.97 | 0.22 | 9 |
| 4.53 | 6.98 | 0.32 | 23 |
| 4.95 | 18.98 | 0.48 | 49 |
| 5.61 | 42.12 | 0.68 | 106 |
| 6.49 | 66.73 | 0.70 | 285 |
| 7.06 | 88.15 | 1.11 | 663 |
| 7.38 | 93.42 | 1.53 | 913 |
| 7.57 | 99.88 | 8.91 | 8509 |

(Note 1)
Percent extraction (%) =

$$\frac{(\text{concentration of the specific metal in the organic phase})}{(\text{concentration of the specific metal in the solution to be extructed prior to the extraction})} \times 100$$

(Note 2)
Co/Ni selectivity coefficient =

$$\frac{[(\text{equilibrium concentration of Co in the organic solvent phase})/(\text{equilibrium concentration of Co in the aqueous phase})]}{[(\text{equilibrium concentration of Ni in the organic solvent phase})/(\text{equilibrium concentration of Ni in the aqueous phase})]}$$

Example 8

Tests were carried out on separation of cobalt ion and nickel ion contained in a waste plating solution comprising following components.

Composition of the waste plating solution

| | | |
| --- | --- | --- |
| nickel (II) | 7.2 | g/L |
| cobalt (II) | 0.5 | g/L |
| sulfate (SO$_4^{2-}$) | 73.1 | g/L |
| hypophosphite (PO$_2^{3-}$) | 39.6 | g/L |
| phosphite (PO$_3^{3-}$) | 140.4 | g/L |
| whole phosphorus | 74.2 | g/L |
| sodium | 84.1 | g/L |
| chelating agent | 46.0 | g/L |
| water | 771 | g/L |

As an extraction solvent, a kerosene solution containing 14.5% by weight of bis(1,1,3,3-tetramethylbutyl)phosphinic was used. The waste plating solution and the extraction solvent were mixed at the volume ratio of 1:1, then stirred at 50° C. for 10 minutes to carry out extraction. The pH of the aqueous phase was controlled by adding ammoniacal water to the waste plating solution prior to the extraction.

The percent extraction of each ion with the pH of the aqueous phase are shown in Table 2.

The percent extraction can be given by the following formula:

Percent extraction (%) =

$$\frac{\text{(concentration of the specific metal in the organic phase)}}{\text{(concentration of the specific metal in the waste plating solution prior to the extraction)}} \times 100$$

TABLE 2

| pH | Nf Extraction rate (%) | Co Extraction rate (%) |
|---|---|---|
| 4.49 | 0 | 31.17 |
| 4.74 | 0 | 45.70 |
| 6.24 | 0.05 | 95.93 |
| 6.64 | 10.35 | 98.84 |

Example 9

As an extraction solvent, a n-hexane solution containing 29.0% by weight of bis(1,1,3,3-tetramethylbutyl)phosphinic acid was used. The waste plating solution and the extraction solvent were mixed at the volume ratio of 1:1, then the mixture was stirred at 23° C. for 10 minutes to carry out extraction. The pH of the aqueous phase was controlled by adding ammoniacal water to the waste plating solution prior to the extraction.

The percent extraction of each ion with the pH of the aqueous phase are shown in Table 3.

TABLE 3

| pH | Ni Extraction rate (%) | Co Extraction rate (%) |
|---|---|---|
| 4.33 | 0 | 25.77 |
| 5.15 | 0 | 75.03 |
| 5.75 | 0 | 92.93 |
| 6.78 | 0.2 | 100 |

Example 10

Extraction was carried out in a manner similar to that of Example 2, except that a n-hexane solution containing 29.0% by weight of bis(1,1,3,3-tetramethylbutyl)phosphinic acid and 10% by volume 1-decanol was used as an extracting agent.

The percent extraction of each ion with the pH of the aqueous phase are shown in Table 4.

TABLE 4

| pH | Ni Extraction rate (%) | Co Extraction rate (%) |
|---|---|---|
| 4.30 | 0 | 18.58 |
| 5.06 | 0 | 56.91 |
| 5.63 | 0 | 78.88 |
| 6.63 | 0 | 93.43 |

Example 11

Extraction was carried out in a manner similar to that of Example 9, except that the extraction was carried out at 50° C. The percent extraction of each ion with the pH of the aqueous phase are shown in Table 5.

TABLE 5

| pH | Ni Extraction rate (%) | Co Extraction rate (%) |
|---|---|---|
| 4.34 | 0 | 47.16 |
| 5.69 | 0 | 97.21 |
| 6.61 | 0 | 100 |

Example 12

As an extraction solvent, a n-hexane solution containing 29.0% by weight of bis(1,1,3,3-tetramethylbutyl)phosphinic acid was used and it was contacted with a waste plating solution and cobalt ion of 0.49 g /L was loaded. The organic phase (solution O) was mixed with an aqueous sulfuric acid solution (solution A, of 0.1 N, 0.2 N, 0.5 N or 1 N at the volume ratio (O/A ratio) of 2:1 to carry out back-extraction. The back-extraction was carried out by stirring the mixture at 21° C. for 30 minutes. The normality of the sulfuric acid, the pH of the resulting mixture when the organic phase was contacted with the sulfuric acid solution, and the percent back-extraction of cobalt ion are shown in Table 6.

TABLE 6

| $H_2SO_4$ conc. in N | pH when contact | Co Back-extraction (%) |
|---|---|---|
| 1 N | 0.75 | 100 |
| 0.5 N | 1.25 | 100 |
| 0.25 N | 2.51 | 66.13 |
| 0.1 N | 5.02 | 0.22 |

The percent back-extraction can be given by the following formula:

Percent back-extraction (%) =

$$\frac{\text{(weight of cobalt ion in the aqueous phase after the back-extraction)}}{\text{(weight of cobalt ion in the organic phase prior to the back-extraction)}} \times 100$$

Example 13

The aged electroless nickel plating solution from which cobalt had been removed according to Example 8 was diluted with pure water so that concentration of nickel was adjusted to about 1 g/liter. n-hexan solution containing 29 wt % of bis(1,1,3,3-tetramethylbutyl)phosphinic acid and 3.1 wt % of di(2-ethylhexyl) phosphate was used as an extraction agent. After adjusting pH of the aged solution with a mineral acid, the extraction agent and the solution were mixed in the volumetric ratio of 1:1, and stirred at 50° C. for 10 minutes. The result is shown in Table 7.

TABLE 7

| pH | Ni Extraction rate (%) | Co Extraction rate (%) |
|---|---|---|
| 5.92 | 52.16 | 0 |
| 6.37 | 62.27 | 0 |
| 7.36 | 82.65 | 0 |

Example 14

The organic solvent phase (di(2-ethylhexyl) phosphate) separated in Example 13, and aqueous solutions of sulfuric acid of concentrations of 0.25 N, 0.5 N and 1 N respectively were mixed in the volumetric ratio, (O):(A)=2:8, and stirred at 21° C. for 30 minutes to carry out a reverse extraction. The result is shown in Table 8.

TABLE 8

| Concentration of sulfuric acid (N) | pH at contact | Ratio of reverse extraction of Ni (%) |
|---|---|---|
| 1 | 2.53 | 100 |
| 0.5 | 3.13 | 100 |
| 0.25 | 4.50 | 59.87 |

What is claimed is:

1. A bis(1,1,3,3-tetramethylbutyl)phosphinic acid compound which is represented by the following general formula (1):

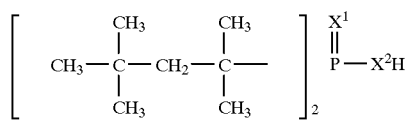

(1)

(wherein $X^1$ and $X^2$ represent an oxygen atom or a sulfur atom, and $X^1$ and $X^2$ can be the same or different).

2. An extracting agent for a metal comprising the bis(1,1,3,3-tetramethylbutyl)phosphinic acid compound according to claim 1.

3. A method of extracting a metal wherein an organic solvent containing an extracting agent comprising the bis(1,1,3,3-tetramethylbutyl)phosphinic acid compound according to claim 1, is contacted and mixed with an aqueous solution containing cobalt and nickel, so that cobalt and/or nickel is extracted into the organic solvent phase and separated from the aqueous solution.

4. A method of separating cobalt contained in an aged electroless nickel plating solution wherein an organic solvent containing an extracting agent comprising a bis(1,1,3,3-tetramethylbutyl)phosphinic acid compound according to claim 1 is contacted and mixed with an aged electroless nickel plating solution containing cobalt and nickel, so that cobalt and/or nickel is extracted and separated from the aged solution into the organic solvent phase.

5. A method of separating cobalt and/or nickel contained in an aged electroless nickel plating solution according to claim 4, wherein the organic solvent phase containing the extracted cobalt and/or nickel is contacted with an aqueous solution containing a mineral acid, so that cobalt and/or nickel is transferred into the aqueous phase by back-extraction and recovered.

* * * * *